United States Patent [19]

Padfield et al.

[11] Patent Number: 4,585,790

[45] Date of Patent: Apr. 29, 1986

[54] PHARMACEUTICAL COMPOSITIONS

[75] Inventors: John M. Padfield, Meldreth; Ian K. Winterborn, Stevenage, both of England

[73] Assignee: Glaxo Group Limited, London, England

[21] Appl. No.: 609,215

[22] Filed: May 11, 1984

[30] Foreign Application Priority Data

May 13, 1983 [GB] United Kingdom ............... 83 13217

[51] Int. Cl.$^4$ ............................................. A61K 31/34
[52] U.S. Cl. .................................................. 514/471
[58] Field of Search ......................... 424/285; 514/471

[56] References Cited

PUBLICATIONS

Chem. Abst. Chem. Sub Index, 97-Ch-Io (1982)-CS2694 98-C-F (1983)-CS 2853.

Primary Examiner—Stanley J. Friedman
Attorney, Agent, or Firm—Bacon & Thomas

[57] ABSTRACT

Aqueous formulations of raniditine have been found to have enhanced shelf life provided that they are formulated with a pH in the range 6.5—7.5. Suitable aqueous formulations include injections for intravenous and intramuscular administration, continuous infusions and oral preparations such as syrups.

13 Claims, No Drawings

PHARMACEUTICAL COMPOSITIONS

The present invention relates to a pharmaceutical composition containing as active ingredient the histamine $H_2$ antagonist ranitidine.

Ranitidine [N-[2-[[[5-(dimethylamino)methyl-2-furanyl]methyl]thio]ethyl]-N'-methyl-2-nitro-1,1-ethenediamine] and its physiologically acceptable salts are described in British Patent Specification No. 1565966. In that specification there is reference to liquid formulations for oral and parenteral administrations and there is a description of an aqueous based formulation for intravenous administration and another of an oral syrup. Both of these formulations contain sufficient hydrochloric acid to achieve a pH of 5.0. In addition injection formulations are described by Padfield et al (The Chemical Use of Ranitidine, Medicine Publishing Foundation Symposium Series 5, Oxford:Medicine Publishing Formulation 1982 pp 18-22) in the form of a simple aqueous solution of ranitidine hydrochloride at its natural pH, i.e. about 5.5. Whilst such formulations containing ranitidine and/or its physiologically acceptable salts are therapeutically effective they suffer from the disadvantage of having a relatively short shelf life due to the breakdown of the ranitidine.

We have now surprisingly found that the shelf life of aqueous based formulations containing ranitidine and/or one or more of its physiologically acceptable salts may be significantly enhanced if the pH of the formulation is adjusted within the range of 6.5-7.5.

Thus the present invention provides a pharmaceutical composition which is an aqueous formulation of ranitidine and/or one or more physiologically acceptable salt thereof, having a pH within the range of 6.5-7.5. The aqueous formulation is prepared using ingredients of a purity such that it is suitable for administration to patients.

The aqueous based ranitidine formulations according to the invention are particularly stable when compared with formulations at a lower pH. Thus for example, in the case of a 25 mg/ml ranitidine hydrochloride injection solution buffered to the appropriate pH with phosphate salts and subjected to storage at 20° C., the rate of breakdown of the ranitidine is about ten times faster for a solution buffered to pH 5.5 than for a solution buffered to pH 7.0.

Conveniently the pH of the formulation according to the invention is adjusted on manufacture within the range 6.5-7.5 by means of the use of suitable buffer salts, for example, potassium dihydrogen orthophosphate and disodium hydrogen orthophosphate or citric acid and disodium hydrogen orthophosphate.

Preferred formulations according to the invention are those wherein the pH is within the range 6.7 to 7.3, for example 6.8 to 7.1.

A preferred embodiment of the invention is an aqueous formulation for parenteral administration. Such a formulation may comprise water suitable for injections in which is dissolved ranitidine and/or one or more of its physiologically acceptable salts and suitable buffer salts. Preferably the solution is adjusted to tonicity by the addition of the appropriate conventional excipients e.g. sodium chloride. Optionally the composition may also contain an antimicrobial preservative, for example phenol.

The concentration of ranitidine in formulations suitable for injection, e.g. intravenous or intramuscular injection is conveniently within the range 10-100 mg/ml, for example 25 mg/ml, expressed as free base. If desired, the solution may be diluted prior to use with, for example, an isotonic saline solution or a dextrose solution. Solutions suitable for continuous infusion may have a concentration of ranitidine of 0.1-2.0 mg/ml, preferably 0.5-1.0 mg/ml, expressed as free base. The solutions for continuous infusion may be presented in this form, for example in packs of 50-100 ml, or may be presented in a more concentrated form, i.e. 10-100 mg/ml, e.g. 25 mg/ml, for subsequent dilution before use, with, for example, an isotonic saline solution or a dextrose solution.

The aqueous formulations for parenteral administration are conveniently prepared by dissolving ranitidine and/or one or more of its physiologically acceptable salts and the excipients in water suitable for injection. The solution, which conveniently is sparged with an inert gas such as nitrogen, is sterilised preferably by filtration and then aseptically packed into suitable containers, e.g. ampoules, vials or containers for infusion, under an atmosphere of nitrogen. Alternatively the formulation may be terminally sterilized, for example by heating.

A further preferred embodiment of the invention is an aqueous formulation for oral administration. Such a formulation may comprise ranitidine and/or one or more of its physiologically acceptable salts dissolved in water, together with buffer salts, a preservative and a viscosity enhancing agent. Optionally the composition may also contain other conventional excipients such as a sweetener, a flavour and/or flavouring aids.

Suitable buffer salts for the oral formulation include potassium dihydrogen orthophosphate and disodium hydrogen orthophosphate or citric acid and disodium hydrogen orthophosphate.

Examples of suitable viscosity enhancing agents include Xanthan gum, sorbitol, glycerol, sucrose or a cellulose derivative such as carboxymethyl cellulose or an ether thereof such as an alkyl and/or a hydroxyalkyl ether of cellulose as for example hydroxypropyl methylcellulose.

Suitable preservatives include the alkyl hydroxylbenzoates, such as methyl, ethyl, propyl and/or butyl hydroxybenzoates.

Suitable sweeteners include saccharin sodium, sodium cyclamate, sorbitol and sucrose.

The concentration of ranitidine in the oral formulation, expressed as free base in conveniently within the range of 20-400 mg per 10 ml, for example 20-200 mg per 10 ml, more particularly 150 mg per 10 ml dose.

The aqueous formulations for oral administration are conveniently prepared by adding an aqueous solution of ranitidine and/or one or more of its salts together with the other excipients to an aqueous solution or dispersion of the viscosity enhancing agent.

The aqueous formulations according to the invention are preferably prepared using ranitidine in the form of its hydrochloride salt.

Illustrative examples of formulations according to the invention are as follows. In these examples the relative proportions of ranitidine hydrochloride and buffer salts are such that each formulation has a pH of approximately 7.

| Raniditine Injection for Intravenous administration (25 mg/ml) | |
| --- | --- |
| Example 1 | mg/ml |
| Ranitidine hydrochloride | 28 |
| Potassium dihydrogen orthophosphate | 0.96 |
| Disodium hydrogen orthophosphate, anhydrous | 2.4 |
| Phenol BP | 5 |
| Water Suitable for Injections BP to | 1 ml |

Ranitidine hydrochloride, the buffer salts and the phenol were dissolved in Water for Injection. The solution was sparged with nitrogen, sterilised by filtration and then aseptically packed into vials under an atmosphere of nitrogen and sealed with a suitable closure.

| Example 2 | mg/ml |
| --- | --- |
| Ranitidine hydrochloride | 28 |
| Potassium dihydrogen orthophosphate | 0.96 |
| Disodium hydrogen orthophosphate, anhydrous | 2.4 |
| Sodium chloride BP | 1.6 |
| Water Suitable for Injections BP to | 1 ml |

An aqueous solution of the ranitidine hydrochloride, the buffer salts and sodium chloride was prepared using Water for Injection. The solution was sparged with nitrogen, sterilised by filtration and then aseptically packed into ampoules under an atmosphere of nitrogen.

| Ranitidine oral liquid formulation (150 mg/10 ml) | |
| --- | --- |
| Example 3 | % w/v |
| Ranitidine hydrochloride | 1.68 |
| Hydroxypropyl methylcellulose | q.s. |
| Parabens (preservative) | q.s. |
| Potassium dihydrogen orthophosphate | 0.095 |
| Disodium hydrogen orthophosphate, anhydrous | 0.350 |
| Sweetening agent(s) | q.s. |
| Flavour | q.s. |
| Purified Water BP to | 100 ml |

A solution of the ranitidine hydrochloride together with the other excipients, except hydroxypropyl methylcellulose, in purified water was added with mixing to a dispersion of the hydroxypropyl methylcellulose in purified water.

| Ranitidine formulations for intravenous infusion. | | |
| --- | --- | --- |
| | Example 4 For a 50 ml Infusion mg/ml | Example 5 For a 100 ml Infusion mg/ml |
| Ranitidine hydrochloride | 1.12 | 0.56 |
| Citric acid BP | 0.3 | 0.3 |
| Disodium hydrogen orthophosphate, anhydrous | 1.8 | 1.8 |
| Sodium chloride BP | 4.5 | 4.5 |
| Water Suitable for Injections BP | to 50.0 ml | to 100.0 ml |

An aqueous solution of the ranitidine hydrochloride, the buffer salts and the sodium chloride is prepared using Water for Injections. The solution is sparged with nitrogen, filled into containers suitable for administering the solution by intravenous infusion, and sterilised by autoclaving.

We claim:

1. A pharmaceutical composition which is an aqueous formulation containing an effective amount of ranitidine and/or one or more physiologically acceptable salts thereof for treatment of conditions mediated through histamine $H_2$-receptors, said formulation having a pH within the range of 6.5–7.5.

2. A pharmaceutical composition according to claim 1 having a pH in the range 6.7 to 7.3.

3. A pharmaceutical composition according to claim 1 having a pH in the range 6.8 to 7.1.

4. A pharmaceutical composition according to claim 1 in which said pH is adjusted by means of suitable buffer salts.

5. A pharmaceutical composition according to claim 4 in which said buffer salts are potassium dihydrogen orthophosphate and disodium hydrogen orthophosphate or citric acid and disodium hydrogen orthophosphate.

6. A pharmaceutical composition according to claim 1 in a form suitable for parenteral administration.

7. A pharmaceutical composition according to claim 6 in a form suitable for injection and containing 10 to 100 mg/ml ranitidine, expressed as free base.

8. A pharmaceutical composition according to claim 6 in a form suitable for continuous infusion and containing 0.1–2.0 mg/ml raniditine, expressed as free base.

9. A pharmaceutical composition according to claim 1 in a form suitable for oral administration.

10. A pharmaceutical composition according to claim 9 containing 20–400 mg per 10 ml dose.

11. A pharmaceutical composition according to claim 1 containing ranitidine in the form of its hydrochloride salt.

12. A process for the production of a composition of claim 1 suitable for parenteral administration, which comprises dissolving ranitidine and/or one or more physiologically acceptable salts thereof and said remaining constituents in water suitable for injection, followed by sterilisation.

13. A process for the production of a composition of claim 1 suitable for oral administration which comprises adding an aqueous solution of ranitidine and/or one or more physiologically acceptable salts thereof to an aqueous solution or dispersion of a viscosity enhancing agent.

* * * * *